United States Patent [19]

Newby et al.

[11] Patent Number: 5,718,239
[45] Date of Patent: Feb. 17, 1998

[54] METHOD OF ACTIVATING A NEEDLE ASSEMBLY HAVING A TELESCOPING SHIELD

[75] Inventors: Mark Newby, Tuxedo, N.Y.; Paul Dicesare, Norwalk, Conn.

[73] Assignee: Becton, Dickinson and Company, Franklin Lakes, N.J.

[21] Appl. No.: 667,680

[22] Filed: Jun. 21, 1996

[51] Int. Cl.$^6$ .................................................... A61M 5/50
[52] U.S. Cl. ................................... 128/763; 604/110
[58] Field of Search ............................. 128/763, 919, 128/764, 765; 604/110, 162, 196, 197, 199

[56] References Cited

U.S. PATENT DOCUMENTS

| | | |
|---|---|---|
| 3,463,152 | 8/1969 | Sorenson . |
| 3,572,334 | 3/1971 | Petterson . |
| 3,595,230 | 7/1971 | Suyeoka . |
| 3,827,434 | 8/1974 | Thompson et al. . |
| 4,160,450 | 7/1979 | Doherty . |
| 4,170,993 | 10/1979 | Alvarez . |
| 4,354,491 | 10/1982 | Marbry . |
| 4,377,165 | 3/1983 | Luther et al. . |
| 4,676,783 | 6/1987 | Jagger et al. ................... 604/171 |
| 4,681,567 | 7/1987 | Masters et al. ................. 604/198 |
| 4,723,943 | 2/1988 | Spencer ......................... 604/198 |
| 4,747,831 | 5/1988 | Kulli ............................ 604/110 |
| 4,781,692 | 11/1988 | Jagger et al. ................... 604/164 |
| 4,804,372 | 2/1989 | Liaco et al. .................... 604/198 |
| 4,826,490 | 5/1989 | Byrne et al. .................... 604/198 |
| 4,867,746 | 9/1989 | Dufresne ........................ 604/192 |
| 4,884,560 | 12/1989 | Kuracina . |
| 4,917,669 | 4/1990 | Bonaldo ......................... 604/164 |
| 4,941,881 | 7/1990 | Masters et al. ................. 604/162 |
| 4,969,876 | 11/1990 | Patterson ....................... 604/171 |
| 4,998,922 | 3/1991 | Kuracina et al. ................ 604/192 |
| 5,084,030 | 1/1992 | Byrne et al. .................... 604/198 |
| 5,112,311 | 5/1992 | Utterberg et al. ............... 604/177 |
| 5,120,320 | 6/1992 | Fayngold ........................ 604/177 |
| 5,185,006 | 2/1993 | Williamitis et al. ............. 604/265 |
| 5,192,275 | 3/1993 | Burns ........................... 604/263 |
| 5,219,333 | 6/1993 | Sagstetter et al. .............. 604/199 |
| 5,254,099 | 10/1993 | Kuracina et al. ................ 604/198 |
| 5,261,880 | 11/1993 | Streck et al. ................... 604/110 |
| 5,266,072 | 11/1993 | Utterberg et al. ............... 604/177 |
| 5,269,765 | 12/1993 | Kuracina ........................ 604/192 |
| 5,290,264 | 3/1994 | Utterberg ....................... 604/263 |
| 5,484,421 | 1/1996 | Smocer .......................... 128/919 |
| 5,536,257 | 7/1996 | Byrne et al. .................... 604/198 |
| 5,549,572 | 8/1996 | Byrne et al. .................... 604/198 |
| 5,601,535 | 2/1997 | Byrne et al. .................... 604/198 |
| 5,616,135 | 4/1997 | Thorne et al. .................. 128/763 |

FOREIGN PATENT DOCUMENTS

| | | | |
|---|---|---|---|
| 0 268 445 | 11/1987 | European Pat. Off. | ......... A61M 5/32 |
| 0 299 287 | 6/1988 | European Pat. Off. | ......... A61M 5/32 |
| WO 89/00865 | 2/1989 | WIPO | ............... A61M 5/00 |

*Primary Examiner*—William E. Kamm
*Assistant Examiner*—George R. Evanisko
*Attorney, Agent, or Firm*—Alan W. Fiedler

[57] ABSTRACT

A method of using a needle assembly having a telescoping shield that extends from a starting retracted position to a venipuncture partially extended position during the standard sequence of operation of drawing a blood sample with an evacuated blood collection tube and needle holder. After the procedure is complete and the needle is removed from the patient the shield continues to extend to a fully extended and locked position over the distal end of the needle rendering the needle safe and preventing needle stick injuries.

9 Claims, 8 Drawing Sheets

METHOD OF ACTIVATING A NEEDLE ASSEMBLY HAVING A TELESCOPING SHIELD

BACKGROUND OF THE INVENTION

1. Field of the Invention

The present invention relates to a safety needle with a telescoping shield that is triggered during a standard sequence of operation of a medical procedure and, more particularly, relates to a needle and hub assembly having a telescoping shield that is triggered when an evacuated tube is mounted in the evacuated tube needle holder.

2. Background Description

An evacuated collection tube, needle and needle holder are commonly used by a doctor, phlebotomist or nurse to draw a sample of body fluid from a patient in a hospital or doctor's office for diagnostic testing. During the use of such a needle holder, the distal end of the needle in the needle holder is inserted in a vein of the patient. The evacuated collection tube is then inserted into the proximal end of the needle holder until a needle within the holder pierces a closure on the end of the tube. The vacuum in the tube then draws a body fluid sample from the patient through the needle and into the tube. After the collection process is complete the needle is removed from the vein and disposed of.

Because of the great concern that users of such needles may be contaminated with the blood of a patient by accidental sticks from the contaminated needle, it is preferable to cover the contaminated needle as soon as it is removed from the vein. For this reason, many developments have been made to provide means for covering the contaminated needle, once it is removed from the patient. These devices usually involve some sort of shield arrangement that moves in place over the contaminated needle once it has been removed from the patient. However, these shield arrangements have required the use of one or two hands to perform the operation of moving the shield over the contaminated needle, which is a hindrance to the user.

Alternatively, needles with internal or external blunting cannulas have been used that extend from the needle to blunt the distal end. However, these devices require an additional manual operation to drive the blunting cannula over or out of the needle upon completion of blood drawing to protect the user from the sharp end of the needle and also allow the user to draw blood without triggering the safety device. Such devices also require the internal diameter of the needle to be decreased which may affect blood flow or require the external diameter of the needle to be enlarged which may cause unnecessary discomfort to the patient.

Other needles have shields that are activated during the venipuncture operation when the shield comes in contact with the skin. Using the skin to activate the device is not desirable since the device may not activate if the needle does not penetrate sufficiently or may cause the shield to inadvertently lock when probing for the vein. Such devices may also require excessive penetration into some patients to cause the triggering means to activate the device which will cause a phlebotomist to unnecessarily have to change their standard method or procedure.

SUMMARY OF THE INVENTION

The present invention overcomes the problems identified in the background material by providing a safety needle incorporating a shield that extends over the distal end of the needle when released by an actuator that is triggered during a standard sequence of operation of a medical procedure.

For example, the safety needle incorporates a telescoping shield that extends by means of a compression spring from a starting retracted position to a venipuncture partially extended position during the standard sequence of operation of drawing a blood sample with an evacuated blood collection tube and needle holder. In particular, when the closure or stopper on the collection tube compresses a rubber multiple sample sleeve on the proximal end of the needle, an actuator is triggered by the closure and/or sleeve to cause the telescoping shield to extend. Then, when the needle is removed from the patient the shield continues to extend to a fully extended and locked position over the distal end of the needle rendering the needle safe and preventing needle stick injuries.

The needle assembly of the present invention consists of a double ended needle cannula having a distal end for venipuncture and a proximal end for puncture of the closure on the evacuated blood collection tube. The needle is retained within a needle hub that attaches to the needle holder and includes the compression spring, an actuator and a telescoping shield. The elastomeric or rubber multiple sample sleeve encompasses the proximal end of the needle cannula. Upon insertion of the evacuated blood collection tube into the needle holder the closure and/or sleeve drives the actuator linearly in the distal direction through a slot in the needle hub. An arm on the distal end of the actuator includes a cam face that engages with a mating surface on a lug at the proximal end of the telescoping shield. The surfaces interact to rotate the shield out of the starting retracted position into a channel whereby the shield is pushed by the compression spring down the length of the cannula to a venipuncture partially extended position. The rotation also loads a torsion spring on the shield to maintain the shield in a loaded/torqued position when at the venipuncture partially extended position. When venipuncture is complete and the needle is withdrawn from the patient, the shield is further extended by the compression spring to the fully extended position. In that position the shield rotates due to the torsion spring to move the lug on the shield from the channel over a ramp and into a distal locking pocket on the needle hub. When the lug is in the locking pocket the shield sufficiently covers the distal end of the needle cannula and renders the needle assembly safe.

An object of the present invention is to provide a needle shield that is automatically activated without having to use one or two hands to perform the shielding operation or an additional action not associated with the normal procedure used during blood collection.

Of course, the present invention is not limited to activation by a blood collection tube since it would be equally functional on a syringe with activation by syringe plunger or on a catheter with activation when the introducer needle is retracted and removed from the catheter device.

These and other aspects, features and advantages of the present invention will become apparent from the following detailed description taken in conjunction with the accompanying drawings.

DETAILED DESCRIPTION

Figure 1:
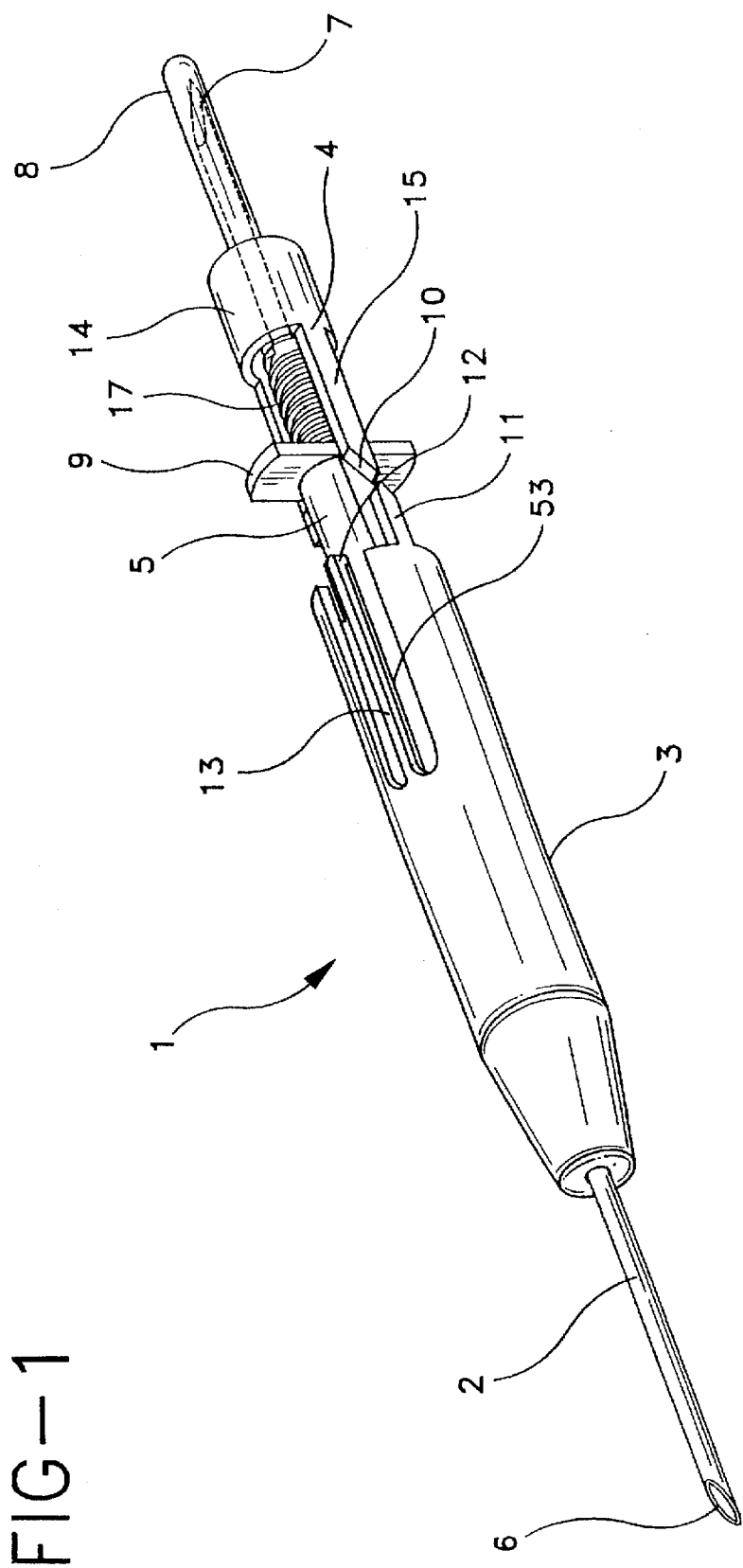
FIG. 1 is a perspective view of a needle assembly according to the present invention in a starting retracted position.

FIG. 1 is a perspective view of a needle assembly 1 according to the present invention in a starting retracted position. Assembly 1 includes a needle cannula 2 mounted in a needle hub 5 having a telescoping shield 3 mounted thereon for movement from a starting retracted position (FIGS. 3 and 7) through a venipuncture partially extended position (FIGS. 4 and 8) to a fully extended and locked position (FIGS. 5 and 9) covering a distal end 6 of needle cannula 2. A proximal end 7 of needle cannula 2 is encompassed by an elastomeric or rubber multiple sample sleeve 8 that is attached to a distal end of needle hub 5 to seal proximal end 7 and prevent fluid from flowing through cannula 2.

Assembly 1 also includes an actuator 4 having a sleeve 14 and a pair of arms 15 that are used to trigger telescoping shield 3 for transport from its starting retracted position to its final fully extended and locked position. As shown in FIG. 1 and described further below, telescoping shield 3 includes a torsion spring 13 having a tab 12 that travels in a longitudinal track 53 on needle hub 5. Shield 3 also includes a pair of lugs 11 that travel in longitudinal channels 54 on needle hub 5 and interact with arms 15 on actuator 4 to trigger movement of telescoping shield 3, when actuator 4 is pushed in the distal direction.

Figure 2:
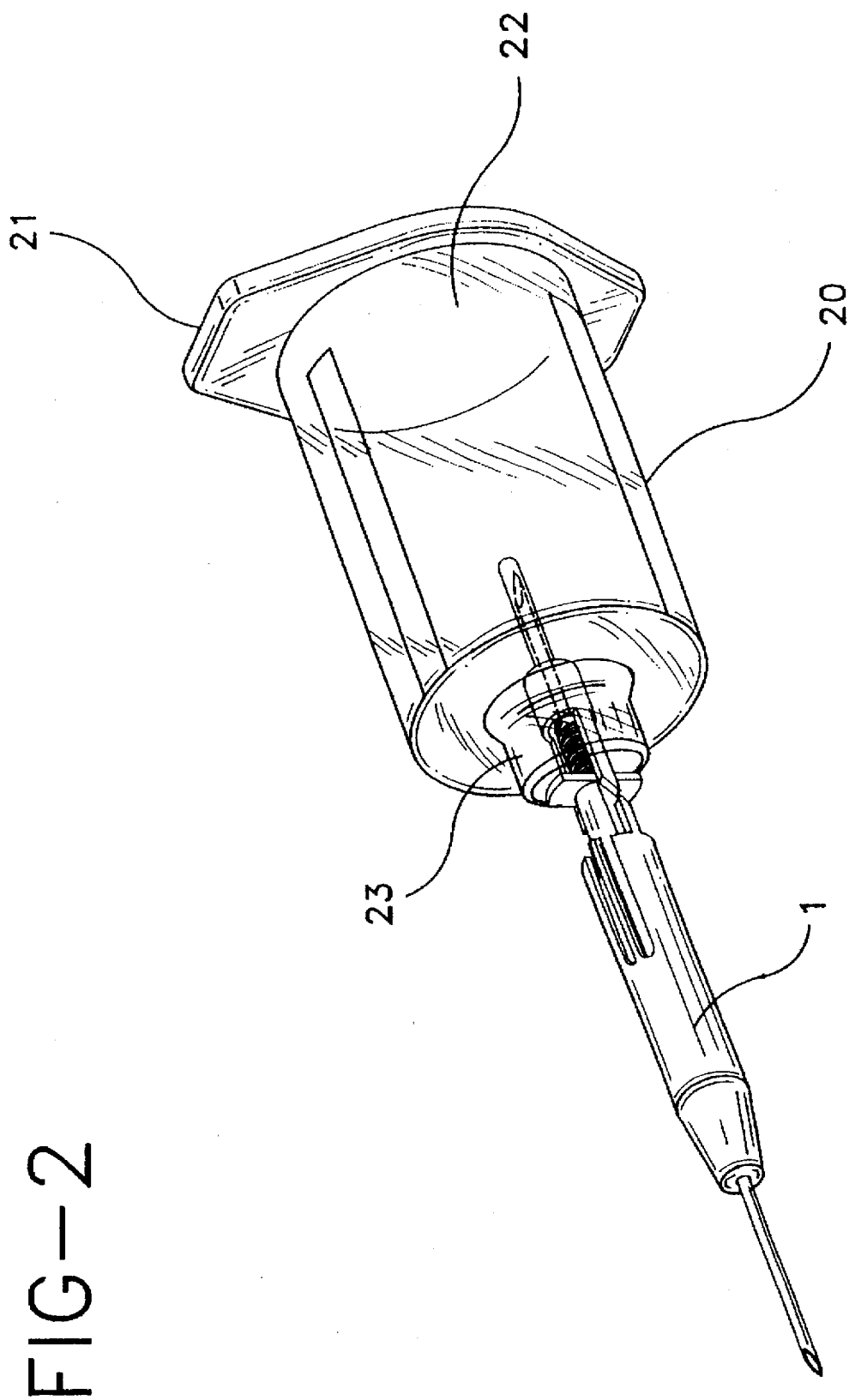
FIG. 2 is a perspective view of the needle assembly shown in FIG. 1 mounted on a needle holder.

FIG. 2 is a perspective view of needle assembly 1 mounted in needle holder 20. Needle holder 20 includes a proximal end 21 and a distal end 23 wherein proximal end 21 includes an opening 22 for receiving an evacuated blood collection tube 50 (FIG. 4) having a closure 51. As more clearly shown in FIG. 3, needle hub 5 on needle assembly 1 includes a flange 9 and a plurality of threads 17 that mate with a plurality of threads 18 in distal end 23 of needle holder 20 to fasten or otherwise attach needle assembly 1 to needle holder 20.

Figure 3:
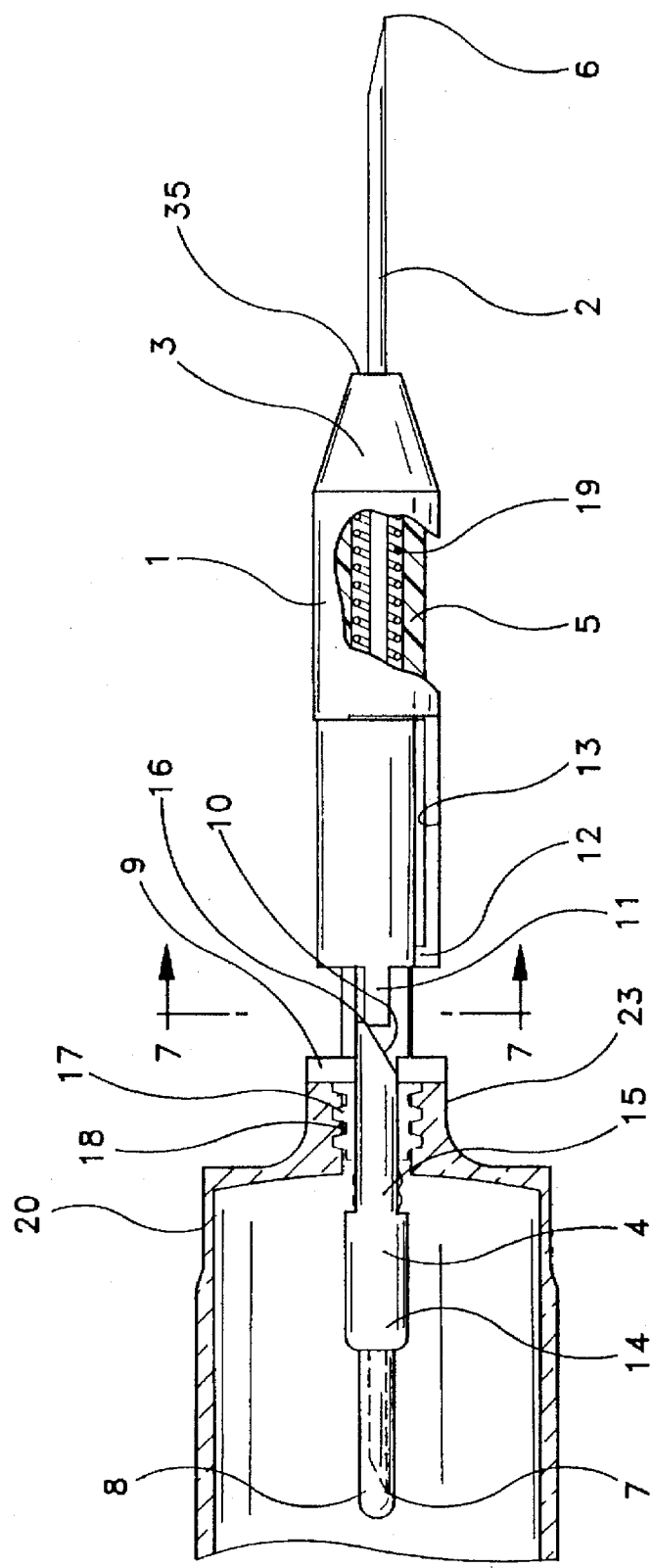
FIG. 3 is a partial cross-sectional view of the needle and holder assembly shown in FIG. 2 in the starting retracted position.

FIG. 3 is a partial cross-sectional view of needle assembly 1 and needle holder 20 with needle assembly 1 in the starting retracted position. In the starting retracted position, cannula 2 extends from a distal end 35 of needle shield 3 so that distal end 6 of cannula 2 is ready for insertion through a patient's skin and into a vein. In the starting retracted position, since no blood collection tube 50 and closure 51 have been inserted into needle holder 20, actuator 4 has not been pushed or moved in the distal direction and shield 3 has not been triggered or activated.

As more clearly shown in FIG. 3, each of arms 15 extending in the distal direction from sleeve 14 on actuator 4 include cam faces 10 that are aligned with and/or adjacent to corresponding mating surfaces 16 on the proximal ends of lugs 11 on shield 3. Cam face 10 and mating surface 16 are arranged to interact with each other to trigger movement of telescoping shield 3 out of the starting retracted position when actuator 4 is pushed in the distal direction. In particular, as actuator 4 is pushed in the distal direction, cam face 10 mates with mating surface 16 to cause lug 11 and shield 3 to rotate in the direction of arrow A in FIG. 7, which allows shield 3 to begin movement down needle hub 5 in the distal direction. The force needed to move or transport shield 3 down needle hub 5 in the distal direction to the venipuncture partially extended position shown in FIG. 4, described below, is provided by a compression spring 19 mounted within needle hub 5.

Figure 4:
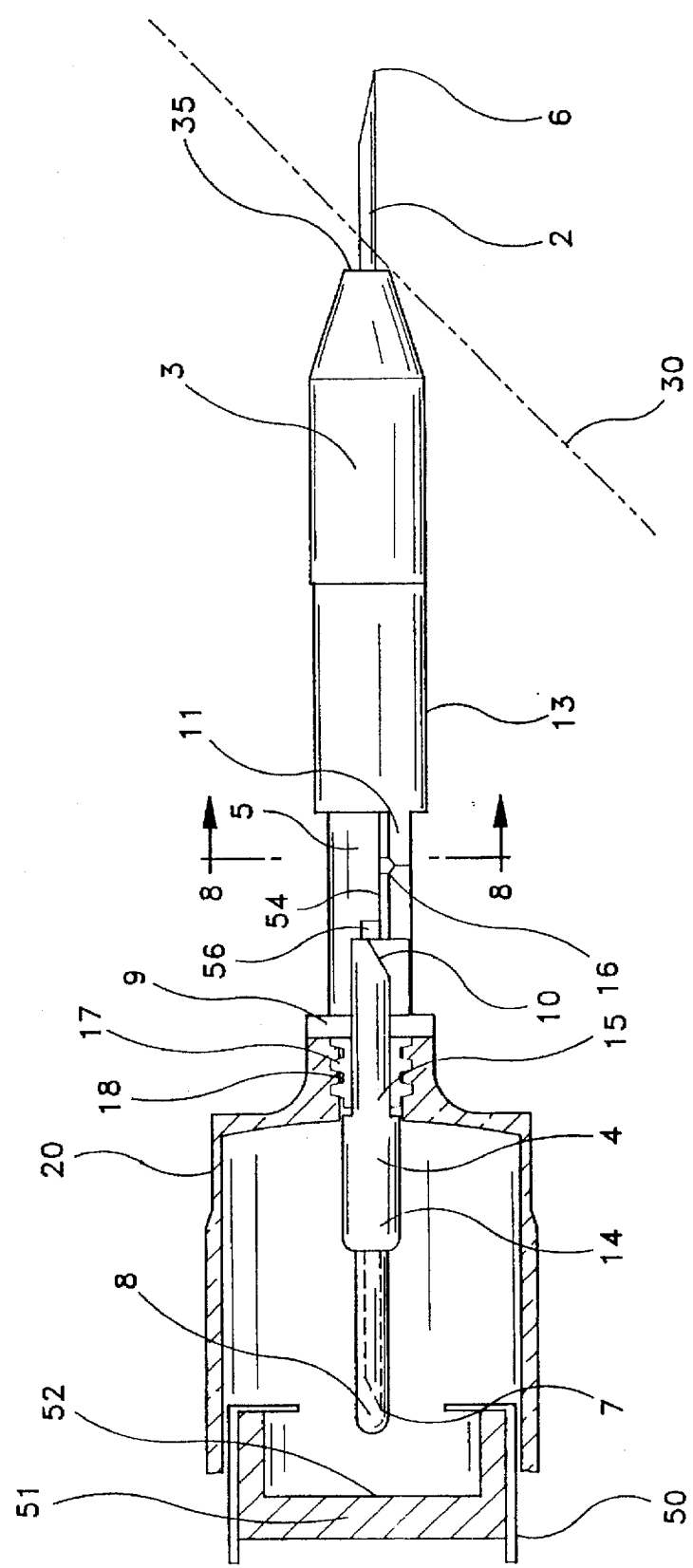
FIG. 4 is a partial cross-sectional view of the needle and holder assembly shown in FIG. 2 in a venipuncture partially extended position.

FIG. 4 shows needle assembly 1 in the venipuncture partially extended position where distal end 6 of needle cannula 2 has punctured a patient's skin 30 and needle assembly 1 has been triggered by movement of actuator 4 in the distal direction. Needle assembly 1 is triggered by the insertion of an evacuated blood collection tube 50 having a closure 51 into needle holder 20, when a top surface 52 of closure 51 compresses multiple sample sleeve 8 after it has been penetrated by proximal end 7 of needle cannula 2. When multiple sample sleeve 8 is compressed by closure 51, sleeve 8 and/or closure 51 interact with and push sleeve 14 of actuator 4 in the distal direction to cause cam surface 10 on arm 15 to mate with mating surface 16 on lug 11 of shield 3. When these surfaces interact, shield 3 is rotated in the direction of arrow A (FIG. 7) and lug 11 is pushed out of a proximal pocket 56 (FIG. 6) in needle hub 5 and into a channel 54 (FIG. 6) in needle hub 5.

After lug 11 has moved into channel 54 compression spring 19 (FIG. 5) transports shield 3 in the distal direction until distal end 35 of shield 3 makes contact with the patient's skin surface 30, as shown in FIG. 4. The phlebotomist can then continue to draw body fluid samples into one or more evacuated collection tubes 50 by easily removing and replacing evacuated tubes 50 until sufficient body fluid has been drawn. The present invention, therefore, permits the user to perform the medical procedure without changing their normal sequence of operation, since no conscious action is needed to activate or otherwise control telescoping shield 3. It should be understood that telescoping shield 3 is triggered and transported to the partially extended position merely by pushing closure 51 onto distal end 7 of cannula 2 and/or compressing multiple needle sleeve 8. After actuator 4 has triggered and transported telescoping shield 3 from the retracted position shown in FIG. 3 to the partially extended position shown in FIG. 4, needle assembly 1 is ready to transport telescoping shield 3 to the fully extended position shown in FIG. 5 when cannula 2 is removed from the patient's skin 30.

Figure 5:
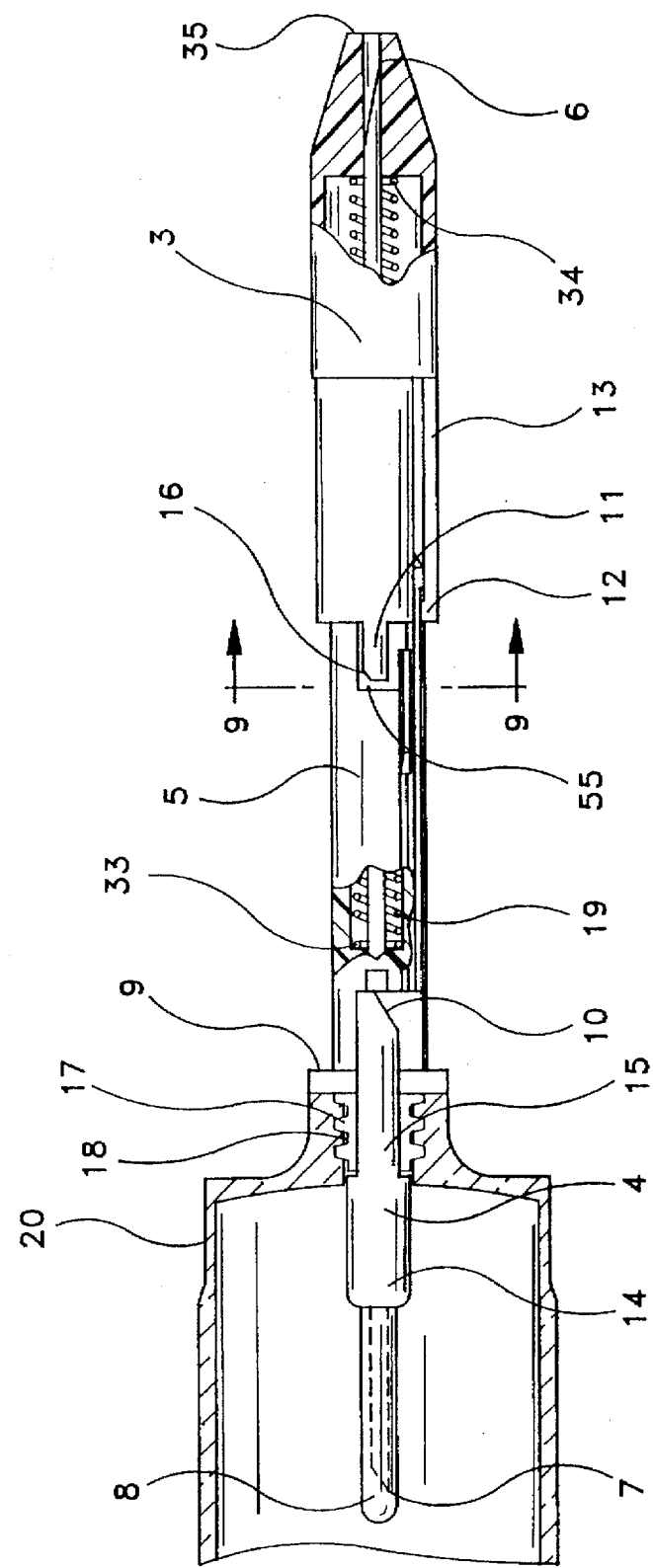
FIG. 5 is a partial cross-sectional view of the needle and holder assembly shown in FIG. 2 in a fully extended and locked position.

FIG. 5 is a partial cross-sectional view of needle assembly 1 and needle holder 20 showing needle assembly 1 in the fully extended and locked position. In this position shield 3 is fully extended such that distal end 35 of shield 3 extends beyond distal tip 6 of cannula 2. FIG. 5 also shows a proximal seat 33 in needle hub 5 and a distal seat 34 in shield 3 for each respective end of compression spring 19 and shows compression spring 19 in its fully extended state where it has fully transported shield 3 from the starting retracted position (FIG. 3) through the venipuncture partially extended position (FIG. 4) and finally to the fully extended and locked position (FIG. 5). FIG. 5 also shows lug 11 located in distal pocket 55 (FIGS. 6 and 9) which together provide means for locking shield 3 in the fully extended position.

Figure 6:
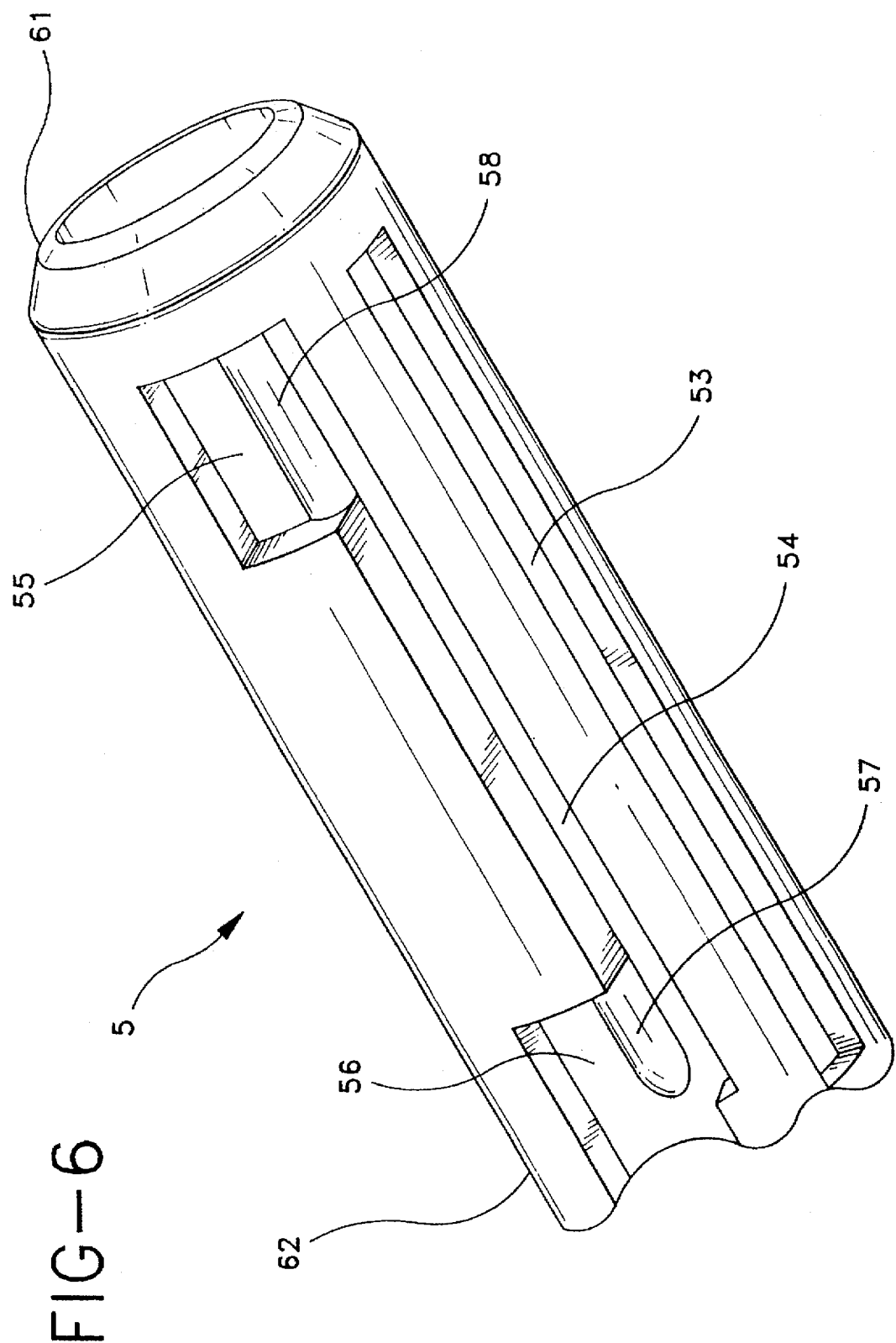
FIG. 6 is a partial perspective view of the needle hub.

FIG. 6 is a partial perspective view of needle hub 5 having a distal end 61 and a proximal end 62. FIG. 6 provides a better view of longitudinal channel 54 and proximal pocket 56 at proximal end 62 and distal pocket 55 at distal end 61. In addition, FIG. 6 shows longitudinal track 53 which is arranged to receive and guide tab 12 on torsion spring 13 as shield 3 moves from the starting retracted position (FIG. 3) through the venipuncture partially extended position (FIG. 4) and finally to the fully extended and locked position (FIG. 5), where torsion spring 13 causes shield 3 to rotate in the direction of arrow B (FIG. 9) and move lugs 11 into their respective distal pockets 55 on needle hub 5.

Figure 7:
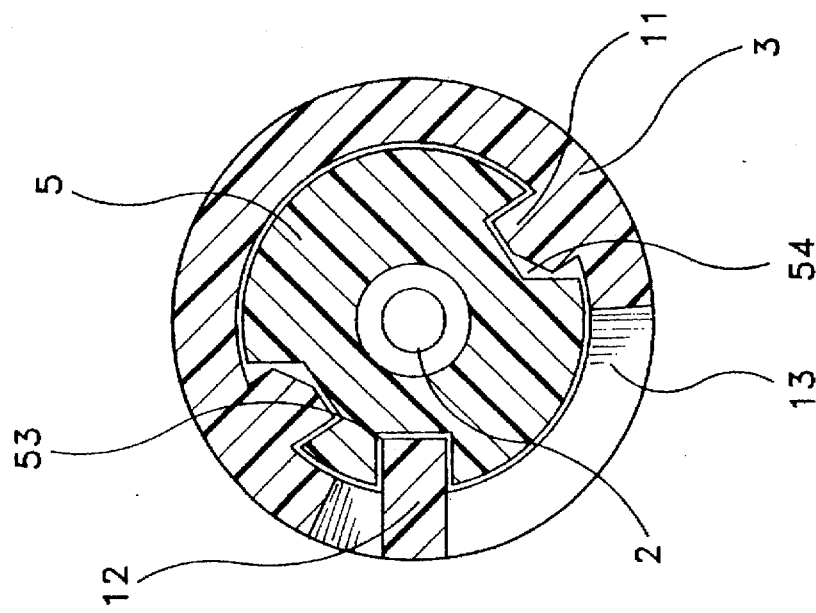
FIG. 7 is a cross-sectional view of the needle assembly shown in FIG. 3 along lines 7—7.
Figure 8:
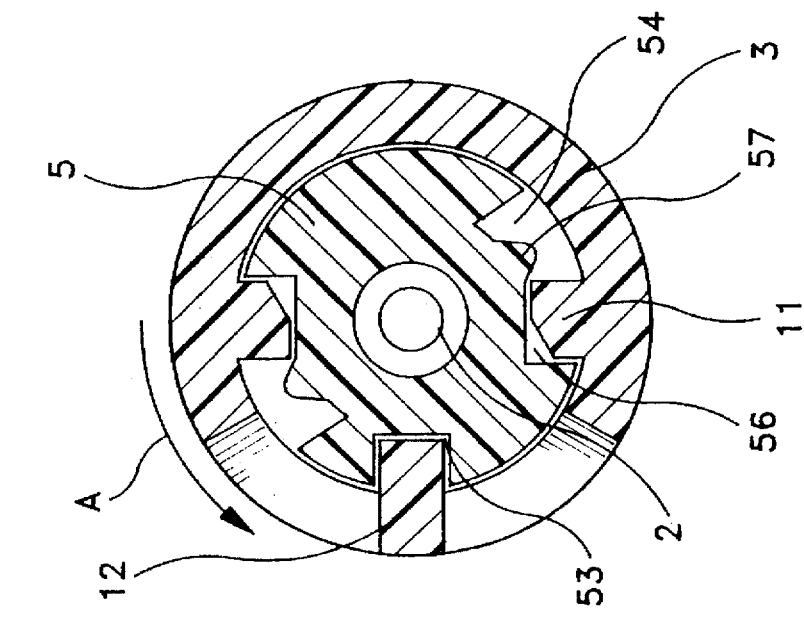
FIG. 8 is a cross-sectional view of the needle assembly shown in FIG. 4 along lines 8—8.
Figure 9:
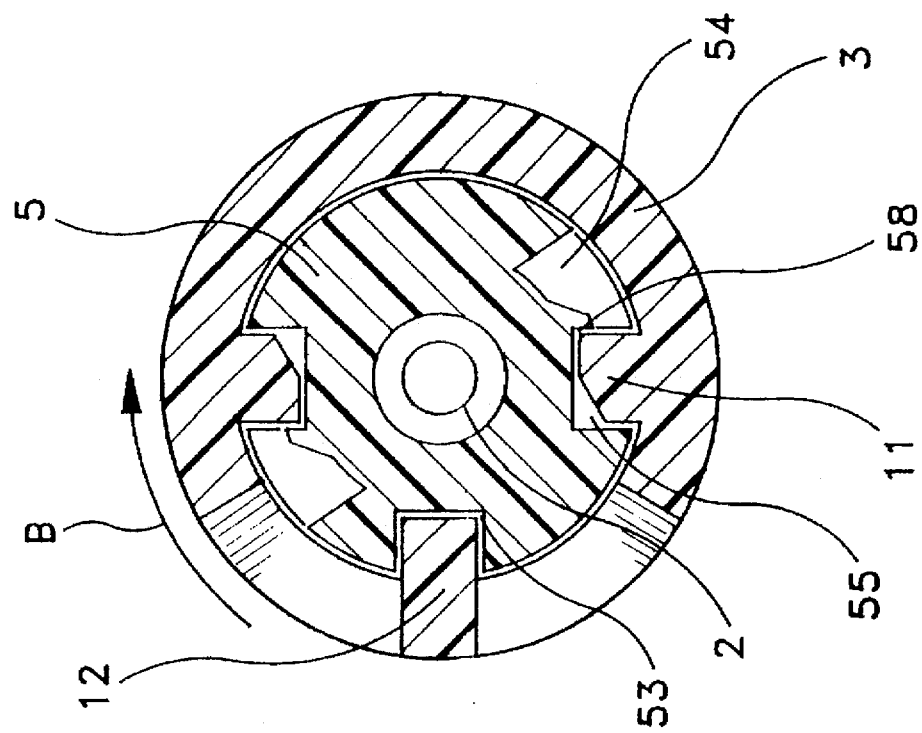
FIG. 9 is a cross-sectional view of the needle assembly shown in FIG. 5 along lines 9—9.

FIG. 7 is a cross-sectional view of needle assembly 1 shown in FIG. 3 at its starting retracted position along lines 7—7. As shown in FIG. 7, tab 12 of torsion spring 13 is located in torsion spring track 53 in needle hub 5 and each shield lug 11 is located in a respective proximal pocket 56. Each of these lugs 11 are held in each pocket 56 by a respective retention rib 57. When closure 51 is penetrated by distal end 7 of cannula 2 and sleeve 14 on actuator 4 causes distal lateral movement of actuator 4 and mating of surfaces 10 and 16, shield 3 is rotated in the direction of arrow A and lugs 11 move over retention ribs 57 into their respective channels 54. Once lugs 11 are in their respective channel 54, compression spring 19 causes distal movement of shield 3 until it reaches the partially extended position shown in FIG. 4. FIG. 8 is a cross-sectional view of needle assembly 1 shown in FIG. 4 along lines 8—8, that more clearly shows lugs 11 in channels 54 and tab 12 of torsion spring 13 in track 53. FIG. 8 also more clearly shows torsion spring 13 under torque due to the rotation of shield 3 in the direction of arrow A.

After venipuncture and withdrawal of cannula 2 from the patient's skin 30, shield 3 moves to its fully extended and locked position shown in FIG. 5. As more clearly shown in FIG. 8, a cross-sectional view of needle assembly 1 shown in FIG. 5 along lines 8—8, each lug 11 is located and locked in a respective distal pocket 55 by a locking ramp 58. In particular, lugs 11 have moved from channels 54 over locking ramps 58 and into distal pockets 55 by rotation of shield 3 in the direction of Arrow B because of the torque on torsion spring 13. FIG. 8 also shows tab 12 on torsion spring 13 located in track 53, but no longer under torque.

Alternatively, rotation of shield 3 would not be needed when distal pocket 55 and proximal pocket 56 are axial with longitudinal channels 54. In such a structure arm 15 on actuator 4 would lift lug 11 out of proximal pocket 56 to trigger movement of shield 3 out of the retracted position. After venipuncture lug 11 would move axially down channel 54 and into distal locking pocket 55 to lock shield 3 in the fully extended position. Torsion spring 13 would not be needed since no rotation is necessary. Of course, other variations could be used and still fall within the scope of the present invention, such as, combining an axial pocket with a pocket requiring rotation.

The above described needle assembly 1 with its telescoping shield 3 is used by a phlebotomist in the following manner and method. After a user has removed needle assembly 1 from its sterile package, it is snap mounted or screw mounted onto distal end 23 of needle holder 20 using threads 17 and 18 until flange 9 comes into contact with distal end 23 of needle holder 20. The user then prepares a venipuncture site on the patient's skin 30 and applies a tourniquet prior to venipuncture.

Venipuncture is then performed by inserting distal end 6 of needle cannula 2 into patient's skin 30 and into a vein. When distal end 6 has been properly inserted and evacuated blood collection tube 50 with its closure 51 is inserted into open end 22 of needle holder 20, closure 51 is then punctured by proximal end 7 of needle cannula 2. When puncture of closure 51 has occurred sufficiently to contact and move actuator 4 in a distal direction, cam face 10 on arm 15 of actuator 4 meets with mating surface 16 on lug 11 of shield 3 to cause shield 3 to rotate in direction A and activate transportation of shield 3 in the distal direction toward the venipuncture site and into the partially extended position.

In addition to activating telescoping shield 3, when proximal end 7 enters into evacuated tube 50 body fluid flows through cannula 2 into evacuated tube 50 and when sufficient body fluid has been received the user can remove evacuated tube 50 from tube holder 20 and continue drawing body fluid with additional evacuated blood collection tubes 50. When evacuated blood collection tube 50 is removed from needle holder 20 multiple sample sleeve 8 returns to its original position to close and seal distal end 7 of cannula 2 and stop the flow of body fluid through cannula 2. When no more body fluid is desired to be collected, needle cannula 2 is withdrawn from the patient's vein and skin 30 permitting shield 3 to further extend to the fully extended and locked position shown in FIG. 5, where distal end 35 of shield 3 extends beyond and sufficiently shields distal end 6 of needle cannula 2.

In the foregoing discussion, it is to be understood that the above-described embodiments of the present invention are merely exemplary. For example, the distal locking pocket can alteratively be located linearly in the channel at the distal end of the needle hub to alleviate the need for rotation by the torsion spring. In addition, of course, the present invention is not limited to activation by a blood collection tube since it would be equally functional on a syringe with activation by syringe plunger rod or on a catheter with activation when the introducer needle is retracted and removed from the catheter device. Other suitable variations, modifications and combinations of the above described features could be made to or used in these embodiments and still remain within the scope of the present invention.

What is claimed is:

1. A method of using a needle assembly having a telescoping shield with an evacuated tube comprising the steps of:

providing a sterile needle assembly comprising a needle cannula mounted in a needle hub and a telescoping shield slidably mounted on the needle hub for movement from a retracted position to a partially extended position and finally to a fully extended and locked position;

providing a needle holder having a distal end for receiving the sterile needle assembly;

mounting the sterile needle assembly on the distal end of the needle holder;· performing a venipuncture by increaing a distal end of the needle cannula into a vein of a patient;

inserting an evacuated tube having a closure into the needle holder;

triggering the telescoping shield to move out of the retracted position to the partially extended position by puncturing the closure on the evacuated tube with a proximal end of the needle cannula;

removing the evacuated tube from the needle holder;

transporting the telescoping shield from the partially extended position to the fully extended position when the distal end of the needle cannula is withdrawn from the vein; and locking the telescoping shield in the fully extended position for safe disposal.

2. A method according to claim 1, wherein said triggering step includes the step of moving the telescoping shield out of the retracted position by pushing the telescoping shield with the closure as the closure is punctured with the proximal end of the needle cannula.

3. A method according to claim 1, wherein said triggering step includes the steps of:

pushing an actuator in the needle assembly with the closure as the closure is punctured with the proximal end of the needle cannula; and moving the telescoping shield out of the retracted position by pushing the telescoping shield with the actuator as it is pushed by the closure.

4. A method according to claim 3, wherein said step of moving the telescoping shield out of the retracted position includes the step of mating a cam face on the actuator with a mating surface on the telescoping shield to move the telescoping shield out of the retracted position.

5. A method according to claim 4, wherein said step of moving the telescoping shield out of the retracted position further comprises the step of moving a lug on the telescoping shield out of a proximal pocket on the needle hub and into a longitudinal channel on the needle hub.

6. A method according to claim 5, wherein said step of locking the telescoping shield in the fully extended position for safe disposal comprises the steps of:

moving the lug on the telescoping shield out of the channel and into a distal locking pocket on the needle hub when the telescoping shield is in the fully extended and locked position; and locking the lug in the distal locking pocket using a retaining ramp located between the distal locking pocket and the channel to prevent the telescoping shield from leaving the fully extended and locked position.

7. A method according to claim 6, wherein said step of moving the lug on the telescoping shield out of the channel and into a distal locking pocket on the needle hub comprises the step of rotating the telescoping shield using a torsion spring mounted on the telescoping shield that causes the lug to move over the retaining ramp and into the distal locking pocket.

8. A method according to claim 1, wherein said step of transporting the telescoping shield from the partially extended position to the fully extended position when the distal end of the needle cannula is withdrawn from the vein comprises pulling the telescoping shield in the distal direction.

9. A method according to claim 1, wherein said step of transporting the telescoping shield from the partially extended position to the fully extended position when the distal end of the needle cannula is withdrawn from the vein comprises pushing the telescoping shield in the distal direction.

* * * * *